(12) United States Patent
Altschul (10) Patent No.: US 7,993,283 B1
(45) Date of Patent: *Aug. 9, 2011

(54) METHOD AND APPARATUS FOR NON-INVASIVE ANALYSIS OF SALIVA

(75) Inventor: Randice Lisa Altschul, Cliffside Park, NJ (US)

(73) Assignee: Pop Test LLC, Cliffside Pakr, NJ (US)

( * ) Notice: Subject to any disclaimer, the term of this patent is extended or adjusted under 35 U.S.C. 154(b) by 110 days.

This patent is subject to a terminal disclaimer.

(21) Appl. No.: 12/380,939

(22) Filed: Mar. 4, 2009

Related U.S. Application Data (63) Continuation-in-part of application No. 12/218,950, filed on Jul. 18, 2008, now Pat. No. 7,824,344.

(60) Provisional application No. 60/951,298, filed on Jul. 23, 2007.

(51) Int. Cl.
*A61B 5/00* (2006.01)
*G01N 21/00* (2006.01)
*G01N 31/22* (2006.01)
*B65D 81/00* (2006.01)

(52) U.S. Cl. ......... 600/573; 600/584; 435/805; 435/810

(58) Field of Classification Search .................. 600/573, 600/580, 582, 584; 422/56–58, 61; 435/287.7, 435/287.8, 287.9, 805, 810, 969, 970, 975; 436/63–71, 808, 810, 823; 206/305, 459.1, 206/459.5, 804, 820, 828

See application file for complete search history.

(56) References Cited

U.S. PATENT DOCUMENTS

| | | | |
|---|---|---|---|
| 1,967,557 A | 7/1934 | John | |
| 5,182,191 A | 1/1993 | Fan et al. | |
| 5,306,623 A * | 4/1994 | Kiser et al. | 435/14 |
| 5,747,351 A * | 5/1998 | Hemmati | 436/514 |
| 5,910,122 A | 6/1999 | D'Angelo | |
| 6,102,872 A | 8/2000 | Doneen et al. | |
| 6,623,698 B2 | 9/2003 | Kuo | |
| 2003/0175993 A1 | 9/2003 | Toranto et al. | |
| 2008/0020477 A1 | 1/2008 | Pronovost | |

* cited by examiner

*Primary Examiner* — Max Hindenburg
*Assistant Examiner* — H. Q. Nguyen
(74) *Attorney, Agent, or Firm* — Arthur Jacob (57) ABSTRACT

A method and apparatus for non-invasive analysis of saliva includes a user friendly lolli-pop like apparatus that is self contained and provides the user with a method to obtain saliva by sucking or licking on the pop head, the saliva activates a color change reaction on the apparatus that results in a color visual response that can be compared to a color coded alphanumeric gauge for analysis in monitoring health conditions and concerns.

19 Claims, 8 Drawing Sheets

FIG. 8 ured in accordance with the present invention is shown.

METHOD AND APPARATUS FOR NON-INVASIVE ANALYSIS OF SALIVA

This application is a Continuation-In-Part of non-provisional patent application Ser. No. 12/218,950 filed on Jul. 18, 2008, now Pat. No. 7,824,344, and claims the priority date of Provisional Application No. 60/951,298 filed Jul. 23, 2007, the substance of which is incorporated herein by reference thereto.

The present invention relates generally to the analysis of saliva through a user friendly lolli-pop like apparatus and pertains, more specifically, to a non-invasive apparatus which can stimulate saliva and result in a color change reaction on the pop, filtered stick, surface area or holding chamber.

The need for self monitoring for a variety of ailments and conditions has grown exponentially over the years. With testing needs ranging from diabetes glucose levels, to alcohol levels to pregnancy, etc. The near epidemic rise in diabetes throughout the World has resulted in a need for a less invasive means of testing glucose levels. Today's methods for testing and monitoring most often result in the user having to provide blood samples to monitor one's condition. The rise in alcoholism and binge drinking has resulted in a need for self monitoring to prevent the need for ambulatory or law enforcement intervention. The increase in drug use both the casual user and the addict has resulted in the need for families as well as the work place and individuals to have a low cost means to monitor the drug use of their people. These are but a few of the applications for usage of this low cost, disposable, user friendly device. As such, the present invention provides several objects and advantages, some of which are summarized as follows: provides a user friendly non-invasive mode for testing which allows the use of a less expensive apparatus suitable for more widespread use and acceptance; enables greater convenience in carrying about and use in testing; allows greater convenience in purchasing; provides a simplified visual mode for monitoring test results; reduces potential hazards of incorrect evaluation of results; enables the economical manufacture and distribution of relatively low-cost, reliable diagnostic test apparatus, thereby opening new and larger markets for testing apparatus.

The above objects and advantages, as well as further objects and advantages, are attained by the present invention which may be described briefly as a non-invasive testing apparatus for analysis of saliva for testing of glucose concentration; pregnancy; alcohol levels; keto levels; or various drug presence. The apparatus may comprise the following components in whole or in part, a means for saliva stimulation; a means for color change activation, ie: a chemical reagent; a filtration to eliminate impurities and a color coded alphanumeric gauge for visual comparison of the results.

The invention will be understood more fully, while still further objects and advantages will become apparent, in the following detailed description of preferred embodiments of the invention in the accompanying drawings, in which.

Figure 1:
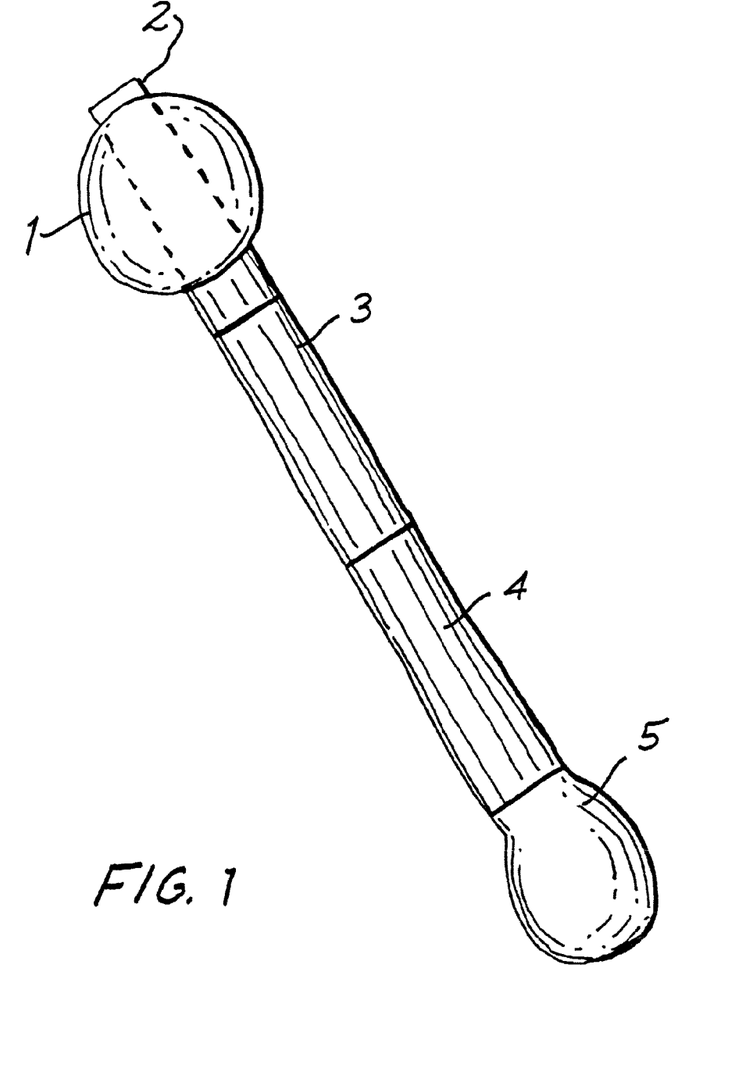
FIG. 1 is a detailed pictorial view of the present invention showing the various embodiments that the testing apparatus can comprise including but not limited to, the reagent pop head, the stem for filter and holding chamber, the bulb base.

Referring now to the drawing and especially to FIG. 1 thereof, an apparatus for non-invasive analysis of saliva constructed in accordance with the present invention is shown. This embodiment includes a lolli-pop like head with a reagent surface 1, saliva stem 2, porous filter a sample of which is a paper, 3, saliva holding chamber 4 and is activated by squeezing suction ball at bottom of stem 5. The user holds the apparatus sucks on the pop head 1, squeezes the suction ball 5, saliva enters the top opening 2, flows through the filter 3 and is housed for color change results in 4 as the saliva interacts with the reagent, and is compared to a color coded alphanumeric gauge.

Figure 2:
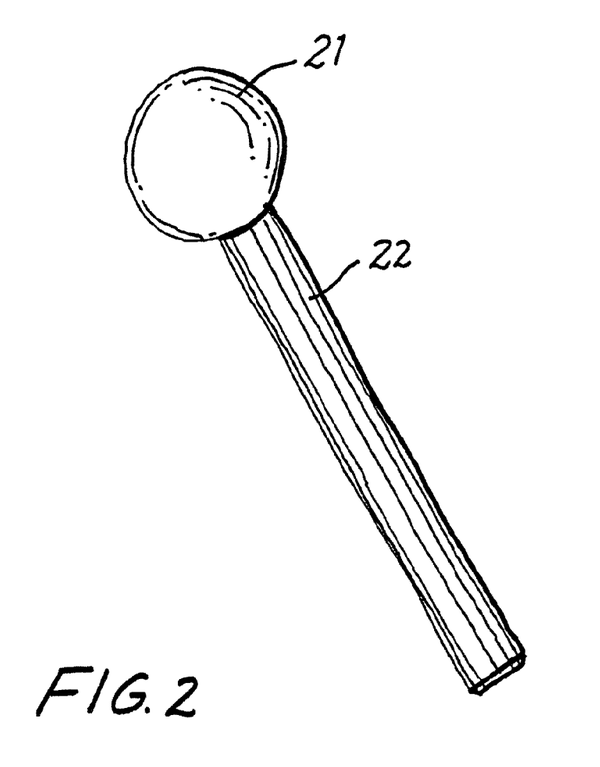
FIG. 2 is a pictorial view showing the testing apparatus with fewer components, just the reagent pop head and stem.
Figure 3:
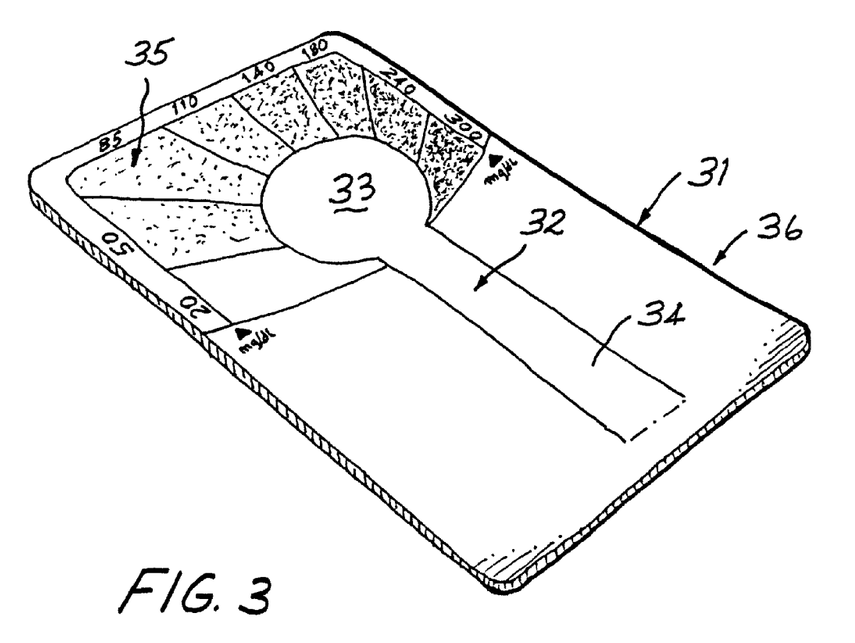
FIG. 3 is a pictorial view showing a compact non-invasive apparatus for the analysis of saliva constructed in accordance with the present invention in flat form with reagent pop head and stem embedded in card surface.
Figure 4:
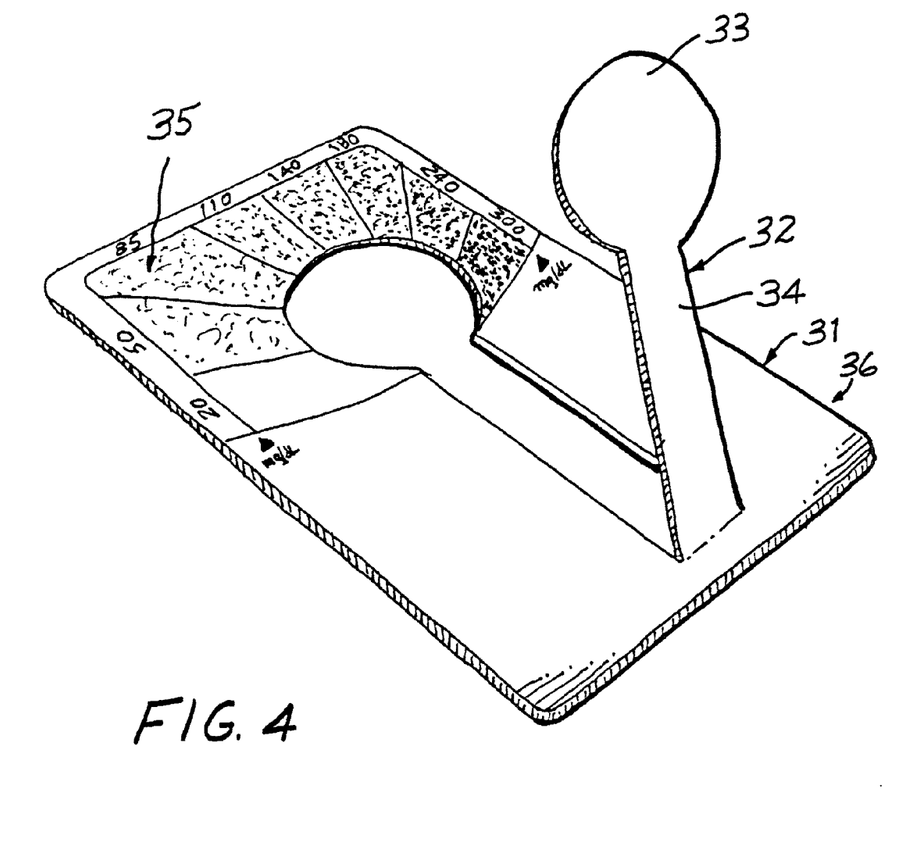
FIG. 4 is a pictorial view showing the method of the apparatus for use as a lolli-pop like test by bending out the head and stem.
Figure 5:
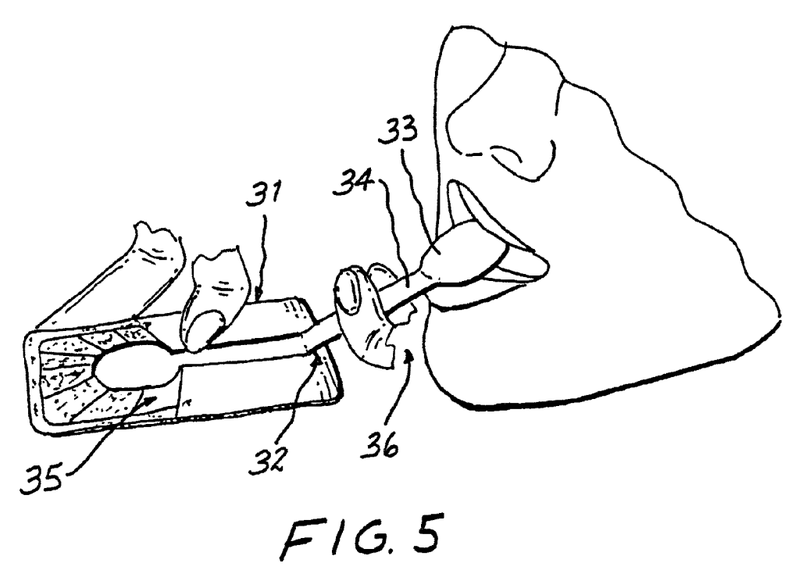
FIG. 5 is a pictorial view showing the method of use of the apparatus by licking the reagent pop head.
Figure 6:
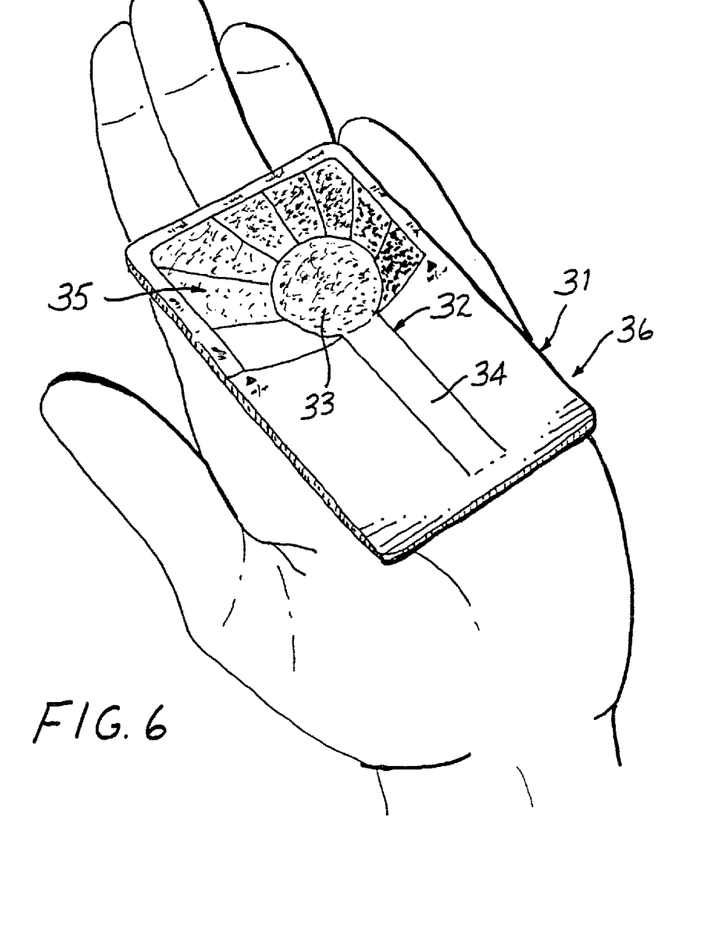
FIG. 6 is a pictorial view showing the results of the saliva test by bending back the reagent pop head and stem to compare to the color coded alphanumeric gauge.
Figure 7A:
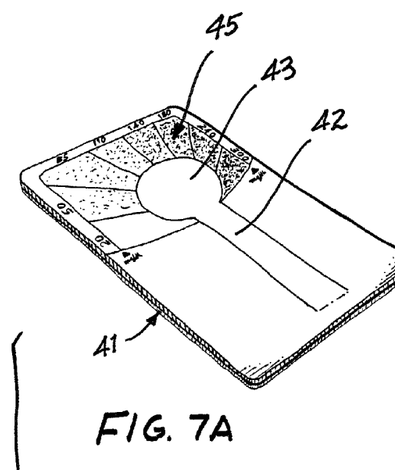
FIG. 7 is a pictorial view showing an embodiment and method of the present invention to avoid oral contact with the reagent surface, with the reagent on the card and the pop head is a porous material like a sponge to absorb saliva and allow saliva to then be pressed onto the reagent surface to compare to the color coded alphanumeric gauge.
Figure 7B:
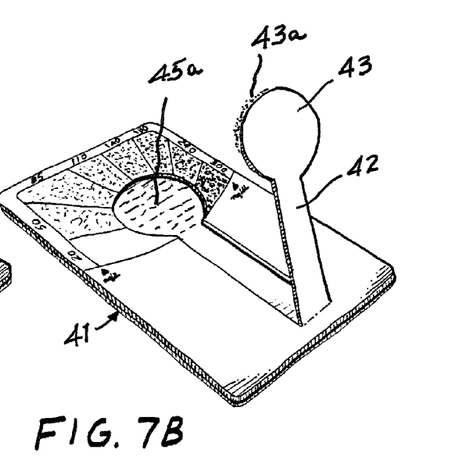
Figure 7C:
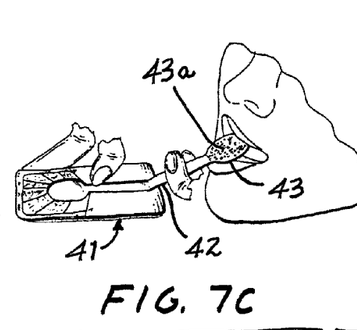
Figure 7D:
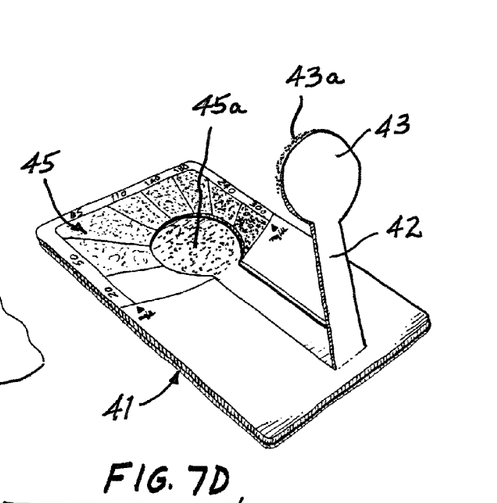

Referring now to the drawing and especially FIG. 2 thereof, an apparatus for non-invasive analysis of saliva constructed in accordance with the present invention is shown. This embodiment includes a lolli-pop with a pop head 21 with a reagent surface and a stem 22. The user holds the stem 22, sucks on the lolli-pop head 21, saliva is stimulated and the head 21 changes color from interaction with the saliva and the reagent, and is compared to a color coded alphanumeric gauge.

Figure 8:
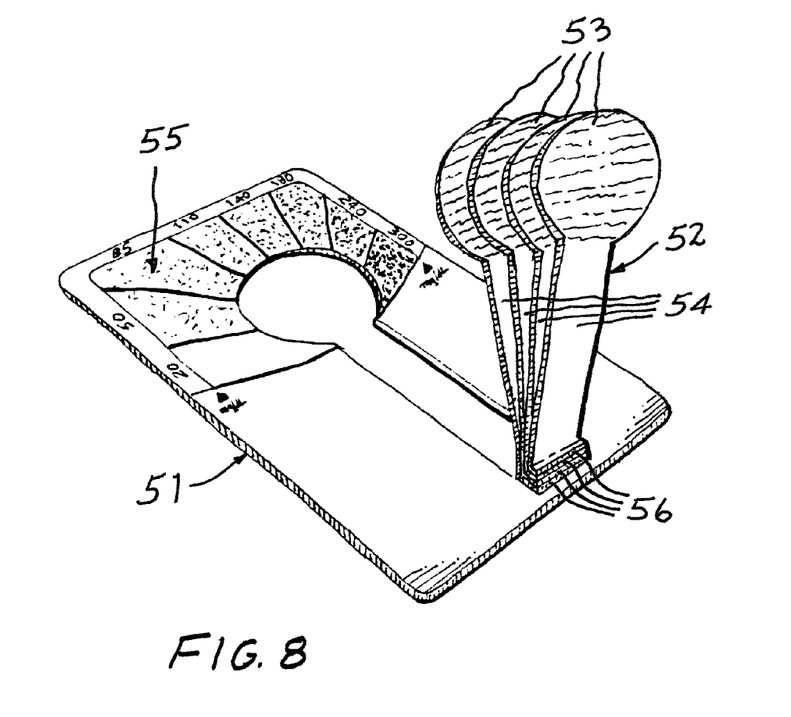
FIG. 8 is a pictorial view showing an embodiment and method of the present invention to allow for multiple lolli-pop test devices to be contained in one apparatus allowing for the disposal of each pop after use to be followed by next available pop built into apparatus.

Turning now to FIGS. 3 through 6, thereof, an apparatus for non-invasive analysis of saliva constructed in accordance with the present invention is shown. This embodiment shows the present invention in a flat form with a die cut lolli-pop like head with a reagent surface, stem, built-in color coded alphanumeric gauge for monitoring results of the test therein, a sampling of the reagents to be used are test specific ie: for glucose testing the reagent chemistry would comprise: glucose oxidose, peroxidase, potassium iodide, non reactive ingredients, buffer and possible color forming substances of mixtures such as tetramethylbenzidine and syringaldazine or impregnated with the enzymes and an oxidizable substrate, orthotolidine; for testing alcohol levels the test reagent chemistry would comprise: Tetramethylbenzidine, alcohol oxidase, peroxidase, buffer and stabilizing proteins; gelatin, water, algin, methyl benzothiazolinone hydrazone hydrochloride, dimethylaminobenzoic acid may also be used; for keto level testing the reagent chemistry would comprise: HBD, NAD, nitroprusside or diazonium salt, a buffer, diaphorase enzyme, sodium nitroprusside, and either NBT or INT and nitrobenzene-diazonium fluoborate; for testing for drug presence the test reagent chemistry would comprise: ion exchange resin, dinitrophenyl an aryl hydrazine, and a stain such as Dragendorff, sodium sulfate, or ninhydrin; for pregnancy testing the reagent chemistry would comprise: is a phenolic derivative of N-acetyl-β-d-glucosamine for reaction to the presence of glucosaminidase at acid pH to allow it to form phenol with a specific color alkaline pH, along with a buffer. Self contained apparatus 31, bend out Lolli-pop 32, pop head 33, stem 34, gauge 35, method of use 36. The user takes the card 31, his method of use 36 is to bend out the lolli-pop apparatus 32, holds onto the stem 34, sucks or licks the lolli-pop head 33, saliva combining with the chemical reagent on the pop results in a color change to head 33, the stem 34, is bent back in place, the pop head 33 color results, is compared to the gauge 35 for analysis. Another embodiment of the present invention FIG. 7 shows the separation of the reagent surface from the pop allowing for the user to be one step away from the chemistry. The pop apparatus 41 bends out lollipop stem 42, licks or sucks pop head 43 which has a saliva absorbing texture a sample of which is a sponge 43a, the pop head 43 and stem 44 is bent back to the apparatus 41 and pressed against the reagent surface 45a to allow the saliva to cause color change on the reagent 45a without the need for the tongue to actually touch the chemistry, to compare to the comparison gauge 45 for results. Turning now to FIG. 8 the present invention is shown with multiple disposable test lollipops 52 each with reagent on pop head 53, attached to multiple stems 54 attached to single card 51 to allow the user to bend out 56 one test pop at a time, test, compare results to gauge 55 then dispose of that pop 52 exposing a new pop 52 ready for next test.

The present invention provides a very compact and practical arrangement for analysis of saliva for health conditions. It will be seen that the present invention attains all of the objects and advantages summarized above, namely: provides a method for monitoring and analysis of saliva which allows the use of a non-invasive low cost apparatus suitable for more widespread use and acceptance; enables greater convenience in monitoring health concerns; allows greater convenience in purchasing and using analysis apparatus; reduces potential hazards associated with incorrect results of saliva analysis; provides greater versatility in the design and function of analysis apparatus; enables the economical manufacture and distribution of low cost, reliable analysis apparatus, thereby opening up new and larger markets for analysis of saliva.

It is understood that the above detailed description of preferred embodiments of the invention is provided by way of example only. Various details of design, chemistry and construction may be modified without departing from the true spirit and scope of the invention, as set forth in the appended claims.

The embodiments of the invention in which an exclusive property or privilege is claimed are defined as follows:

1. An apparatus for conducting a non-invasive analysis of saliva to determine the presence and the level of a certain constituent carried by the saliva, the apparatus comprising:
   a flat card-like device having a flat configuration resembling a relatively thin card, the device including a base;
   a visible gauge on the base, the visible gauge including an interpretation site and visible regions of different colors displayed upon the base adjacent the interpretation site;
   a lolli-pop-like structure including a stem integrated with the base and a head integrated with the stem, the stem including a finger-grip, and the head including a receptor for the reception of a saliva sample;
   the receptor being constructed of a material having a saliva-absorbing texture;
   the stem being selectively pivoted by a user out of the flat configuration for placement at a first position wherein the head is spaced away from the base for placement of the head in juxtaposition with the user's mouth to facilitate reception of the saliva sample in the receptor, and wherein the stem extends away from the base to expose the finger-grip for gripping by the user, and is pivoted subsequently to a second position wherein the stem is retracted toward the base and the head is inserted into the flat configuration to place the receptor of the head at the interpretation site, confined in juxtaposition with the visible gauge; and
   a reagent carried by one of the head at the receptor and the base at the interpretation site, the reagent being capable of changing color in response to exposure to the certain constituent, such that upon placement of the stem in the first position, the finger-grip is available for gripping by the user, with the receptor exposed for receiving the saliva sample, and upon subsequent placement of the stem in the second position, the receptor is juxtaposed with the interpretation site, confined within the base, so that any change in color of the reagent in response to exposure of the reagent to the saliva sample will be visibly registered in side-by-side contiguity with the regions of different colors of the visible gauge for enabling a direct visual comparison of the change in color of the reagent with a corresponding color of a visible region of the visible gauge, thereby providing a directly readable indication of the presence and the level of the certain constituent in the saliva sample.

2. The apparatus of claim 1 wherein the analysis of the saliva sample is for a level of glucose concentration, and the reagent consists essentially of glucose oxidase and peroxidase, a buffer, a mixture of tetramethylbenzidine and syringaldazine, and non-reactive ingredients.

3. The apparatus of claim 1 wherein the analysis of the saliva sample is for a level of alcohol, and the reagent consists essentially of alcohol oxidase and peroxidase, a buffer, a stabilizer, tetratmethylbenzidine, and at least one of the group consisting of algin, methyl benzothiazolinone hydrazone hydrochloride, and dimethylaminobenzoic acid.

4. The apparatus of claim 1 wherein the analysis of the saliva sample is for a level of keto, and the reagent consists essentially of diaphorase, sodium nitroprusside, a buffer and at least one of the group consisting of nitroprusside and diazonium salt.

5. The apparatus of claim 1 wherein the analysis of the saliva sample is for the presence of a drug, and the reagent consists essentially of an ion exchange resin, at least one of the group consisting of dinitrophenyl and aryl hydrazine, and a stain selected from the group consisting of Dragendorff and ninhydrin.

6. The apparatus of claim 1 wherein the analysis of the saliva sample is for determining pregnancy, and the reagent consists essentially of a buffer and a phenyl derivative of N-acetyl-beta-D-glucosamine resulting from reaction to the presence of N-acetyl-beta-D-glucosaminidase at acid pH to yield phenol with a specific color alkaline pH.

7. The apparatus of claim 1 including a plurality of lolli-pop-like structures integrated with the base.

8. The apparatus of claim 1 wherein the lolli-pop-like structure is die-cut within the base and is bent out of and back into the base for use, and the gauge includes alphanumeric characters to enable calibration of the results of a particular saliva sample analysis.

9. The apparatus of claim 1 wherein the material of the receptor is an absorbent sponge like material.

10. The apparatus of claim 1 wherein the reagent is carried by the receptor.

11. The apparatus of claim 1 wherein the reagent is carried by the base at the interpretation site.

12. A method for conducting a non-invasive analysis of saliva to determine the presence and the level of a certain constituent carried by the saliva, the method comprising:
- providing a flat card-like device having a flat configuration resembling a relatively thin card, the device including a base;
- providing a visible gauge on the base, the visible gauge including an interpretation site and visible regions of different colors displayed upon the base adjacent the interpretation site;
- providing a lolli-pop-like structure including a stem integrated with the base and a head integrated with the stem, the stem including a finger-grip, and the head including a receptor for the reception of a saliva sample, the receptor being constructed of a material having a saliva-absorbing texture;
- pivoting the stem out of the flat configuration to a first position wherein the head is spaced away from the base to locate the head in juxtaposition with a user's mouth for facilitating reception of the saliva sample in the receptor, and wherein the stem extends away from the base to expose the finger-grip for gripping by the user;
- subsequently pivoting the stem to a second position wherein the stem is retracted toward the base and the head is inserted into the flat configuration to place the receptor of the head at the interpretation site, confined in juxtaposition with the visible gauge; and
- providing a reagent carried by one of the head at the receptor and the base at the interpretation site, the reagent being capable of changing color in response to exposure to the certain constituent, such that upon placement of the stem in the first position, the finger-grip is available for gripping by the user, with the receptor exposed for receiving the saliva sample, and upon subsequent placement of the stem in the second position, the receptor is juxtaposed with the interpretation site, confined within the base, so that any change in color of the reagent in response to exposure of the reagent to the saliva sample is visibly registered in side-by-side contiguity with the regions of different colors of the visible gauge for enabling a direct visual comparison of the change in color of the reagent with a corresponding color of a visible region of the visible gauge, thereby providing a directly readable indication of the presence and the level of the certain constituent in the saliva sample.

13. The method of claim 12 wherein the analysis of the saliva sample is for a level of glucose concentration, and the reagent consists essentially of glucose oxidase and peroxidase, a buffer, a mixture of tetramethylbenzidine and syringaldazine, and non-reactive ingredients.

14. The method of claim 12 wherein the analysis of the saliva sample is for a level of alcohol, and the reagent consists essentially of alcohol oxidase and peroxidase, a buffer, a stabilizer, tetratmethylbenzidine, and at least one of the group consisting of algin, methyl benzothiazolinone hydrazone hydrochloride, and dimethylaminobenzoic acid.

15. The method of claim 12 wherein the analysis of the saliva sample is for a level of keto, and the reagent consists essentially of diaphorase, sodium nitroprusside, a buffer and at least one of the group consisting of nitroprusside and diazonium salt.

16. The method of claim 12 wherein the analysis of the saliva sample is for the presence of a drug, and the reagent consists essentially of an ion exchange resin, at least one of the group consisting of dinitrophenyl and aryl hydrazine, and a stain selected from the group consisting of Dragendorff and ninhydrin.

17. The method of claim 12 wherein the analysis of the saliva sample is for determining pregnancy, and the reagent consists essentially of a buffer and a phenyl derivative of N-acetyl-beta-D-glucosamine resulting from reaction to the presence of N-acetyl-beta-D-glucosaminidase at acid pH to yield phenol with a specific color alkaline pH.

18. The method of claim 12 wherein the reagent is provided carried by the head at the receptor.

19. The method of claim 12 wherein the reagent is provided carried by the base at the interpretation site.

* * * * *